(12) United States Patent
Willhelmus et al.

(10) Patent No.: US 7,852,182 B2
(45) Date of Patent: Dec. 14, 2010

(54) PENDULUM DRIVE SYSTEM FOR PERSONAL CARE APPLIANCES

(75) Inventors: Ettes Willhelmus, Leeuwarden (NL); Pawel Leshem, Drachten (NL); Pieter Johannes Bax, Drachten (NL); Andries Bron, Drachten (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 122 days.

(21) Appl. No.: 11/997,762

(22) PCT Filed: Aug. 4, 2006

(86) PCT No.: PCT/IB2006/052704
§ 371 (c)(1),
(2), (4) Date: Feb. 4, 2008

(87) PCT Pub. No.: WO2007/017823
PCT Pub. Date: Feb. 15, 2007

(65) Prior Publication Data
US 2008/0204177 A1 Aug. 28, 2008

Related U.S. Application Data

(60) Provisional application No. 60/706,121, filed on Aug. 5, 2005.

(51) Int. Cl.
*H01F 7/08* (2006.01)
*H01F 5/00* (2006.01)

(52) U.S. Cl. ...................... 335/220; 335/266

(58) Field of Classification Search ............. 335/220, 335/228, 229, 235, 243, 252, 256, 266, 90, 335/87, 93; 310/15, 21
See application file for complete search history.

(56) References Cited

U.S. PATENT DOCUMENTS

| | | | | | |
|---|---|---|---|---|---|
| 2,089,334 | A | * | 8/1937 | Bredehoft | 310/29 |
| 2,759,114 | A | * | 8/1956 | Klett et al. | 310/29 |
| 3,042,843 | A | * | 7/1962 | Edwards et al. | 335/230 |
| 3,113,251 | A | * | 12/1963 | Morel et al. | 335/229 |
| 3,121,194 | A | * | 2/1964 | Stehlik | 335/230 |
| 3,296,468 | A | | 1/1967 | Chambrey | |

(Continued)

FOREIGN PATENT DOCUMENTS

CH 609238 2/1979

(Continued)

*Primary Examiner*—Elvin G Enad
*Assistant Examiner*—Alexander Talpalatskiy

(57) ABSTRACT

The actuator (10, 90) of a personal care appliance, such as a toothbrush (11), which includes a housing member (12), a double E shaped yoke assembly (14, 52) with two electrical coils (36, 38) wound around the opposing E shaped sections. An armature (28) extends adjacent the top of the yoke assembly (14, 52), extending beyond the edges thereof. The armature (28) further includes side portions which extend adjacent the sides of the E shaped yoke (52), with each side portion including two spaced magnets which are aligned with the coils (36, 38) when the actuator (10, 90) is in a rest position. Power is supplied from a battery source, and a programmable control assembly (46) applies power to the coils (36, 38) in a selected manner to produce axial and/or tangential or complex movement of the brushhead workpiece (33) at the end of an output shaft extending from the armature (28).

11 Claims, 7 Drawing Sheets

U.S. PATENT DOCUMENTS

| | | | |
|---|---|---|---|
| 3,538,359 A * | 11/1970 | Barowski | 310/29 |
| 3,987,255 A * | 10/1976 | Kawakami et al. | 310/15 |
| 4,363,980 A * | 12/1982 | Petersen | 310/15 |
| 4,392,092 A * | 7/1983 | Gassner | 318/127 |
| 4,675,563 A * | 6/1987 | Goldowsky | 310/15 |
| 5,896,076 A * | 4/1999 | van Namen | 335/229 |
| 6,184,597 B1 * | 2/2001 | Yamamoto et al. | 310/14 |
| 6,657,326 B1 * | 12/2003 | Yamamoto et al. | 310/12.27 |
| 6,954,040 B2 * | 10/2005 | McGill et al. | 318/127 |
| 7,288,863 B2 * | 10/2007 | Kraus | 310/37 |
| 2002/0129454 A1 * | 9/2002 | Hilscher et al. | 15/22.1 |
| 2002/0163701 A1 * | 11/2002 | Plesko | 359/199 |
| 2002/0195884 A1 * | 12/2002 | Ichii et al. | 310/15 |
| 2004/0010871 A1 * | 1/2004 | Nishinaka et al. | 15/22.2 |
| 2004/0128781 A1 * | 7/2004 | Kunita et al. | 15/22.2 |
| 2005/0127759 A1 * | 6/2005 | Kraus et al. | 310/36 |

FOREIGN PATENT DOCUMENTS

| | | |
|---|---|---|
| EP | 294760 | 7/1988 |
| FR | 1081323 | 12/1954 |
| JP | 2001268880 | 9/2001 |
| JP | 2004194499 | 9/2001 |
| WO | 2005062445 | 7/2005 |

* cited by examiner

PENDULUM DRIVE SYSTEM FOR PERSONAL CARE APPLIANCES

CROSS REFERENCE TO RELATED APPLICATION

This application claims the benefit of U.S. provisional application Ser. No. 60/706,121 filed Aug. 5, 2005, which is incorporated by reference.

This invention relates generally to drive systems (actuators) for personal care appliances, such as electric toothbrushes, and more specifically concerns such a drive system which uses magnetic action to produce movement of a workpiece mounting shaft in the X-Y plane.

In personal care appliances, such as electric toothbrushes, shavers, trimmers and similar devices, it is important to have a reliable drive (actuating) system which provides the desired movement of the workpiece. Other factors, such as expense, ease of assembly and safety, are also important relative to such actuating systems.

Many different types of drive/actuating systems are known, including small motors, both AC and DC, and various magnetic and electromagnetic arrangements. Most actuating systems, however, are designed to produce a single, particular type or mode of movement of the workpiece, usually either a tangential movement, such as rotation or partial rotation, or axial movement, such as an in-and-out vibration. In some cases, however, it is desirable to have an actuating system which can produce more than one mode of movement of the workpiece. In other cases, it is desirable to have an actuating system which can produce a more complex movement of the workpiece, involving the simultaneous use of two separate modes of movement to produce a complex movement, such as for instance, a figure-eight or similar pattern. A programmable capability is desirable, such that workpiece motion of an appliance can be conveniently changed, to accommodate special uses.

Accordingly, the actuator includes an actuator mechanism for a personal care appliance having a housing, comprising: a yoke assembly having two or more spaced outer coil support legs and an intermediate workpiece support leg; an armature positioned adjacent the free ends of the leg portions of the yoke assembly; a spring assembly connecting the armature to the housing of the personal care appliance; an output drive shaft extending from the armature member adapted to receive a workpiece mounting shaft and/or a workpiece member at a free end thereof; at least one coil wound on two coil support legs of the yoke assembly; a source of power for the actuator mechanism; and a programmable control system for applying power to the coils in a selected manner to move the armature and the output drive shaft in at least two dimensions.

FIGS. 1 and 2 show one embodiment of a drive system referred to herein as a pendulum actuator, generally at 10, for use in personal care appliances, such as a toothbrush 11.

Figure 1:
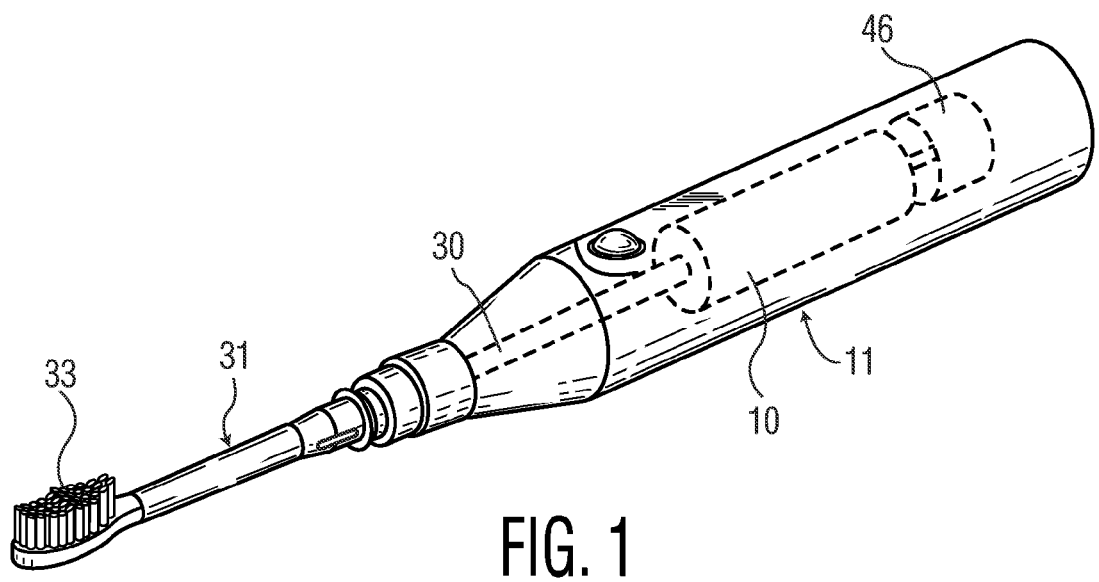
FIG. 1 shows a toothbrush which incorporates the drive system of the present invention.

Actuator 10 includes a housing 12 and an E shaped yoke 14 mounted within housing 12. Yoke 14 includes two outer legs 16, 18, an intermediate leg 20 and a base member 40. At the top of intermediate leg 20 is a notch or depression 24, which is adapted to receive a mating protrusion 26 which depends from the center of the lower surface of a plate-like armature 28. Armature 28 extends outwardly to the outer edges of outer legs 16 and 18 of the E shaped yoke 14 and is positioned slightly above the free ends of the legs. Other yoke shapes, including D shaped and others, could be used in addition to the E shaped yoke.

Secured to the upper surface of armature 28 is a mounting block 29 from which extends an output shaft 30, which drives a workpiece mounting shaft 31 (FIG. 1) at the end of which is attached a workpiece, such as a toothbrush brushhead 33.

Armature 28 is supported relative to the E shaped yoke 14 by spring assemblies 34 34 which extend between mounting block 29 (on yoke 14) and housing 12. With the spring assembly support, the armature and the output shaft are able to both move together axially relative to the E shaped yoke and the housing and to tilt in one direction or the other relative to intermediate leg 20 of the E shaped yoke. Wound around the outer legs 16 and 18, respectively, of the E shaped yoke 14 are coils 36 and 38. Coils 36 and 38 extend approximately from base member 40 of the E shaped yoke 14 to near the top of the outer legs 16 and 18.

The above arrangement results in the amplitude of displacement of the armature 28 (and the output shaft 30 and hence workpiece shaft 31 and workpiece 33) in the "Y" plane (toward and away from yoke 14) being independent of several structural and physical parameters of the drive system as a whole, including the distance between the armature 28 and the yoke 14, and the spring constant of both springs 34, among others.

Figure 2:
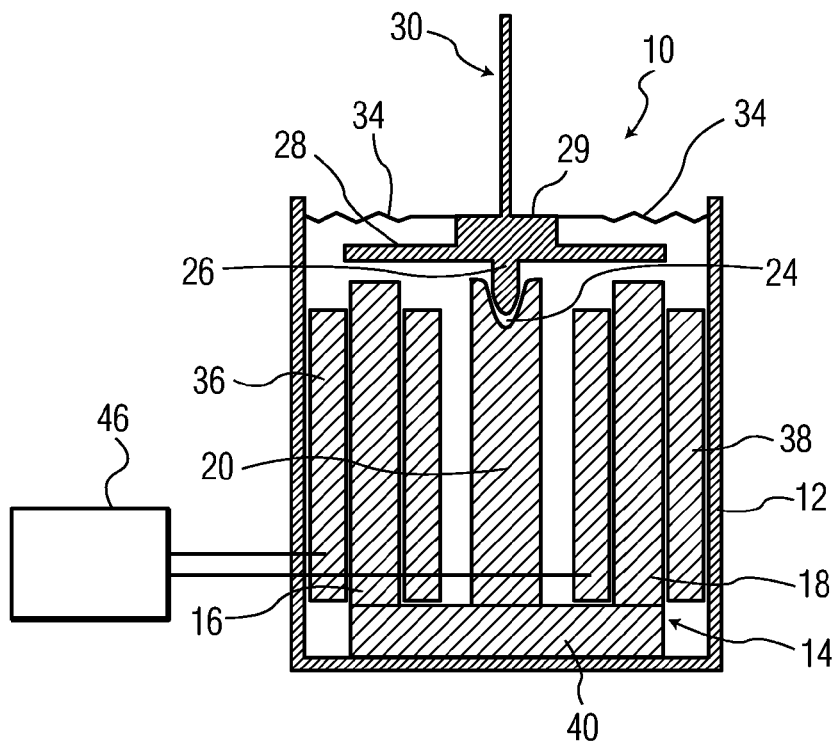
FIG. 2 is a longitudinal cross-sectional view of one embodiment of the actuator.

Referring to FIG. 2, the air gaps shown between the armature 28 and the E shaped yoke 14 must be small. Otherwise, the force of attraction will be small. This would result in a rather limited longitudinal (axial) displacement of the armature (and ultimately the workpiece) in the X Y plane.

Figure 3:
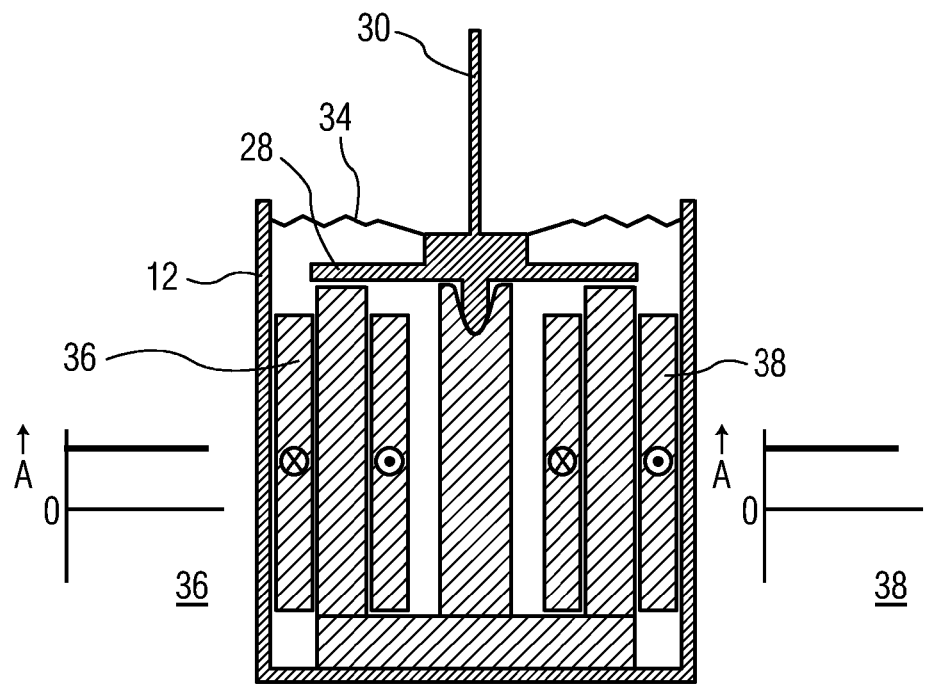
FIG. 3 shows one mode of movement of the actuator of FIG. 2.

A programmable power/control unit 46 provides electric power to the two coils. In the present case, electric power is provided by a battery. The control unit 46 controls the application of power to one or both of the coils. With the arrangement shown, if electric currents with equal magnitude are directed through both coils 36 and 38, the armature 28 and the output shaft 30 with the workpiece on shaft 31 will move axially toward the E shaped yoke 14. This is illustrated in FIG. 3. Hence, an axial, back-and-forth movement of the workpiece can be programmed by simply applying equal magnitude electric current pulses periodically to the coils.

Figure 4A:
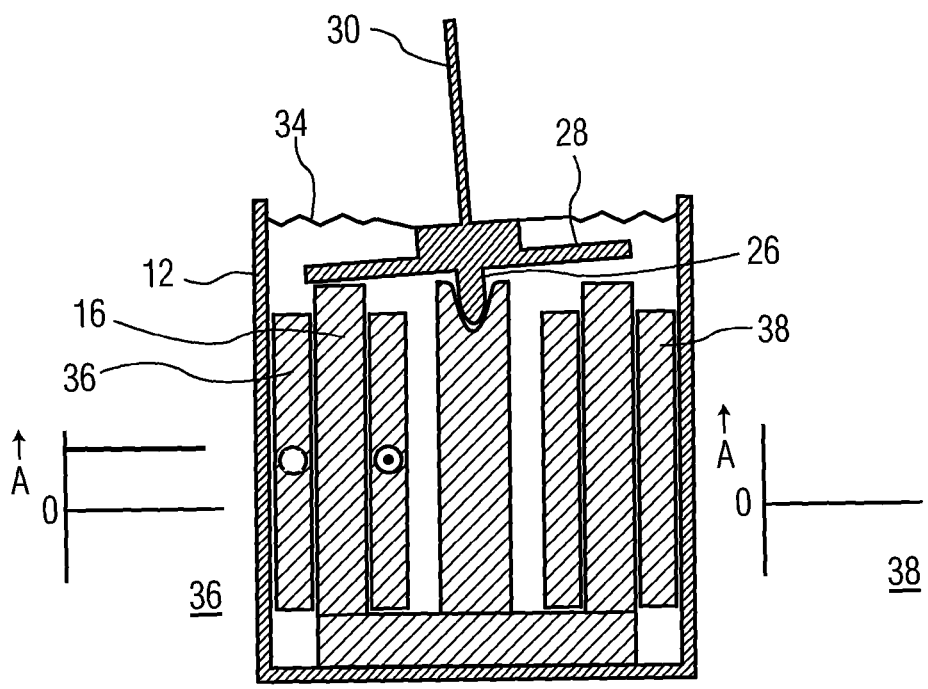
FIGS. 4A and 4B show other movements of the actuator of FIG. 2.
Figure 4B:
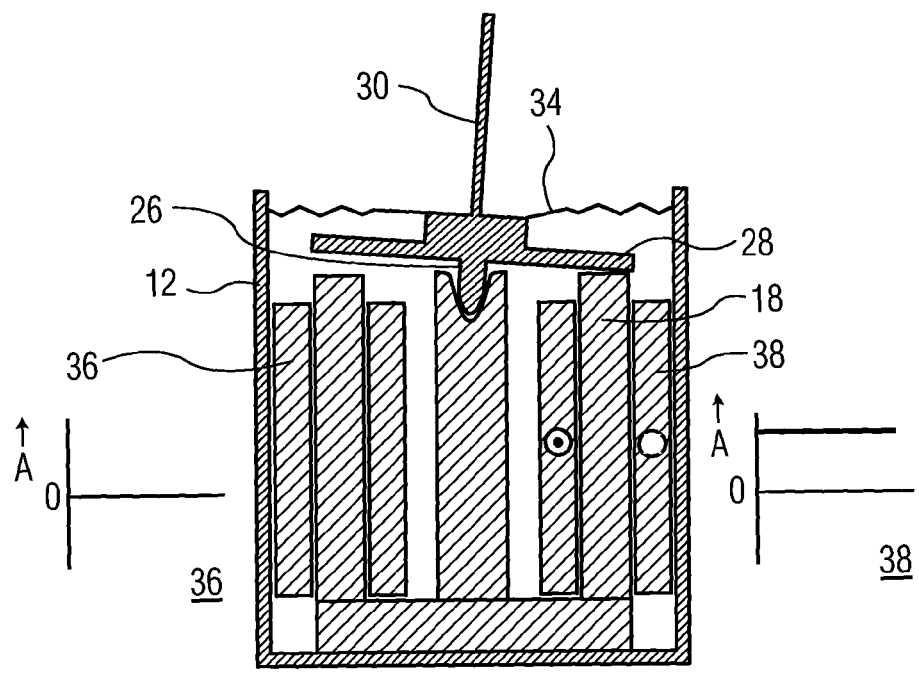

If an electric current is applied to coil 36 only, as illustrated, the armature 28 and the drive shaft will move (tilt) toward that portion of the E shaped yoke, producing a linear movement of the workpiece in the "X" plane, as shown in FIG. 4A. Alternatively, if current is applied to coil 38 only, the armature and the drive shaft will tilt toward that portion of the E shaped yoke, as shown in FIG. 4B.

Further, if an AC modulation is applied to the DC current applied to coils 36 and 38, complex waveforms resulting in complex movement of drive shaft 30 and the workpiece mounted on shaft 31 are possible.

As indicated above, alternative yoke configurations are possible, such as D shaped and/or other shapes. Also, the yoke could have more than two (e.g. 3 or 4) legs to support coils.

Further, in some embodiments, one coil or more than two coils could be used. The movement of the actuator can be in three dimensions as well as just X and Y dimensions.

FIGS. 5, 6A, 6B and 7A, 7B show another embodiment of the pendulum actuator. This embodiment also includes a housing 50, a double (back-to-back) E shaped yoke 52 (although other yoke configurations can be used) which is mounted within housing 50, and an armature 54 extends over the top and down the opposing sides of yoke 52. The side portions 56, 57 of armature 54 each include a pair of spaced permanent magnets mounted on an interior surface thereon, extending toward the E shaped yoke 52. The magnets on one side portion 56 are 58 and 60, while the magnets on the other side portion are 62 and 64. The magnets have polarity indications (N/S) as shown. Spring members 66 and 68 connect the top ends 67, 69 of the side portions 56, 57 of the armature to the housing 50, while spring members 70 and 72 connect the lower ends 71, 73 of the side portions of the armature 54 to the housing.

Mounted to the top surface 79 of the armature 54 at the center thereof is a mounting block 75, from which extends a drive shaft 77, similar to that shown in the embodiment of FIG. 2. The free end of shaft 77 will typically connect to a workpiece shaft 31, at the end of which is a workpiece, such as a toothbrush brushhead, as shown in FIG. 1.

Wound around one of the E shaped sections of yoke 52 is a first coil 76, and wound around the opposing E shaped section is a second coil 78. A different number of coils can be used, including one coil, depending on the arrangement of the yoke. The magnets 58 and 60 are aligned adjacent the first coil 76 while magnets 62 and 64 are aligned with the second coil 78, when the actuator is in a rest (unactivated) position. Electrical power is provided by a programmable power control unit 80.

Figure 5:
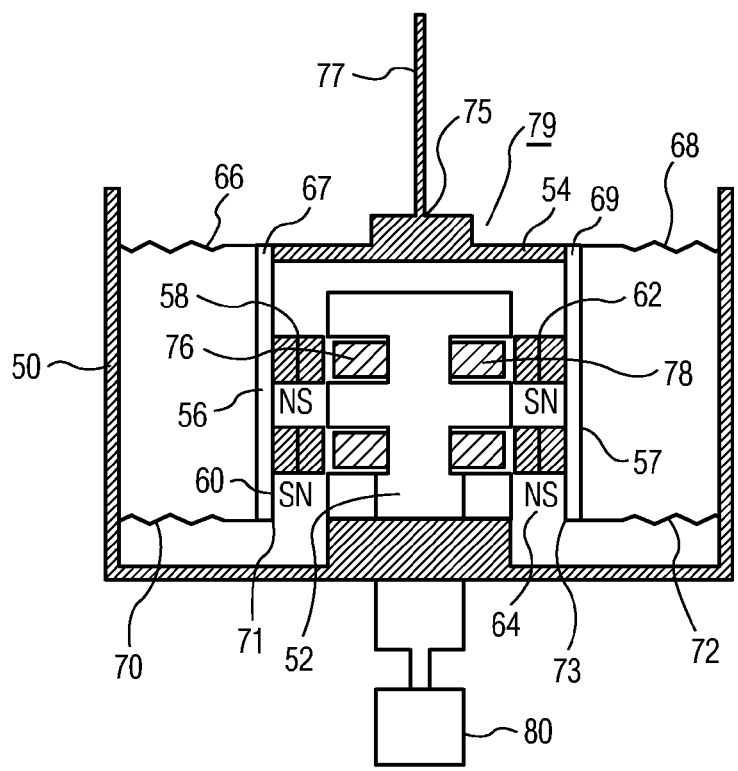
FIG. 5 is a cross-sectional view of another embodiment of the actuator.

The advantage of the arrangement of FIG. 5 is that the displacement of armature 54 and ultimately the workpiece is not dependent upon the initial air-gap distance between the armature and the yoke. Rather, factors such as the magnetic cross-section of the yoke, the magnitude of the applied current, the strength of the permanent magnets, and the spring constant of the four springs determines the action of the actuator.

The arrangement of FIG. 5 produces a more symmetrical actuation and hence more efficient operation than the embodiment of FIG. 2. Two-dimensional and three-dimensional movements are possible with this embodiment. When a current is applied by the power circuit 80 through coils 76 and 78 in the directions, indicated in FIG. 6A, an attraction force results between the upper magnets 58 and 62 and the upper portions of the coils 76, 78 and a repulsion force results between the lower magnets 60 and 64 and the lower sections of coils 76, 78. Armature 54 moves away from its rest position and away from the yoke 52, as shown by the indication of upward movement of the armature in FIG. 6A.

Figure 6A:
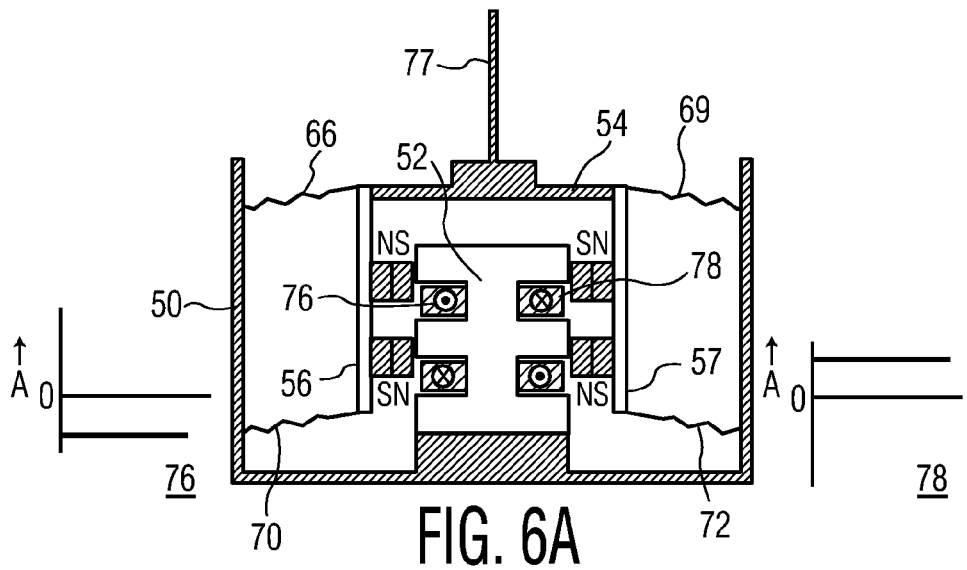
FIGS. 6A and 6B and 7A and 7B show various movements of the actuator of FIG. 5.
Figure 6B:
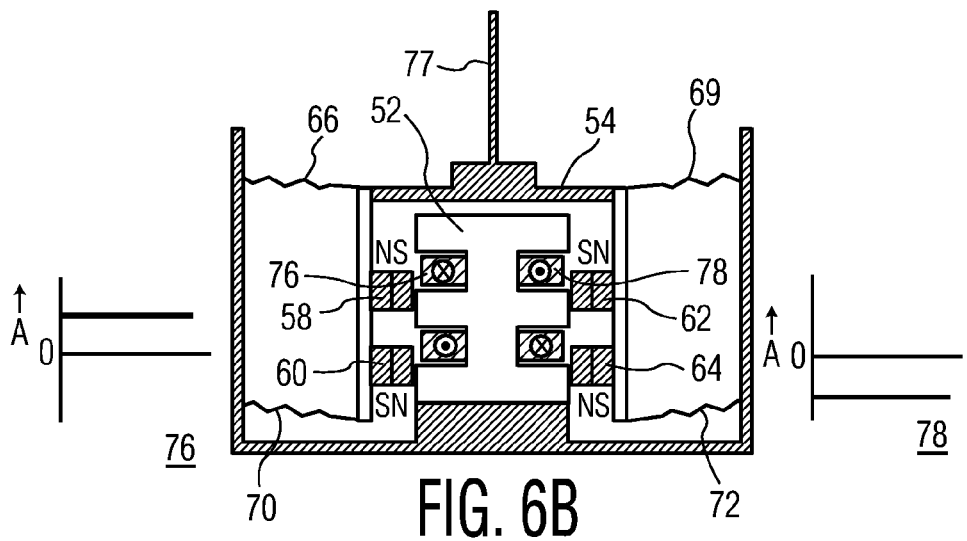

Conversely, when the currents through coils 76 and 78 are reversed, flowing in the opposite direction from that shown in FIG. 6A, the armature will move toward yoke 52, as shown in FIG. 6B. This dual movement provides for an axial (in-and-out) movement in the Y plane of the armature and the mounting shaft (with the workpiece).

Figure 7A:
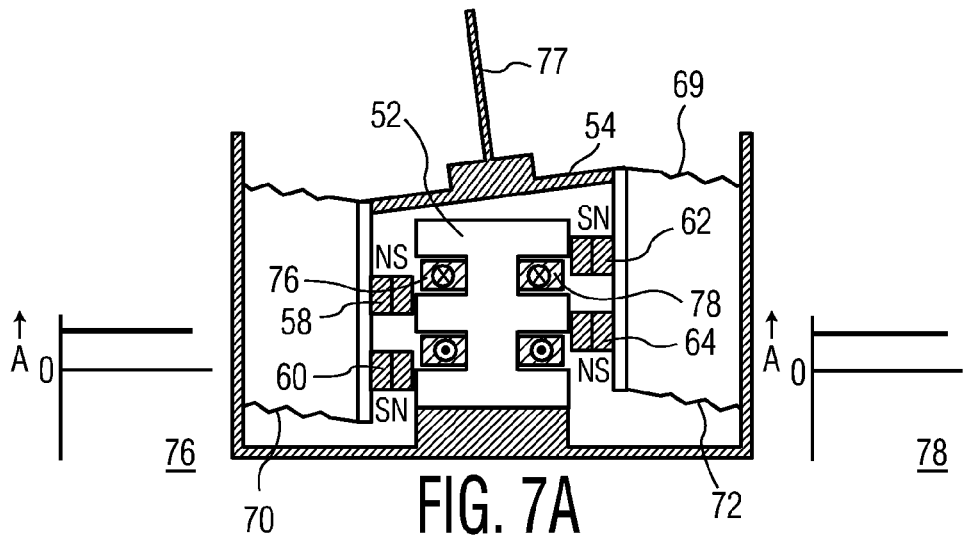
Figure 7B:
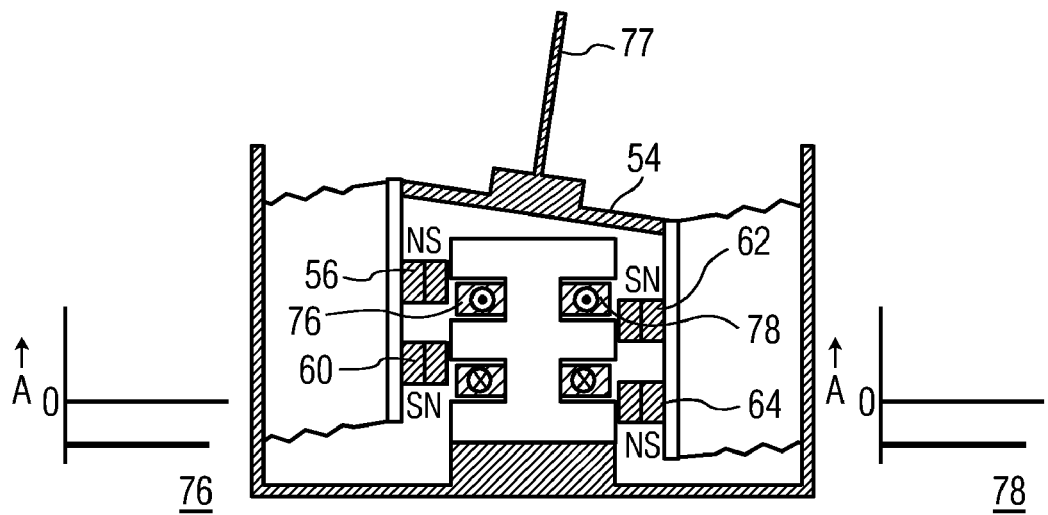

If a current is applied through only one coil, e.g. coil 76 only, or through both coils in the same direction, the armature 54 will tilt in one direction, as shown in FIG. 7A, producing a linear movement in the "X" plane. The opposing movement is accomplished by a current flow through coil 78 only, or currents through both coils in the same direction but opposite to that of FIG. 7A. This is shown in FIG. 7B.

Thus, by changing the direction of the current through coils 76 and 78, the armature can be moved both axially and tangentially. By AC modulating the current through the two coils, complex waveforms of the output shaft 77 are possible, with both amplitude and frequency being programmable, resulting in both two-dimensional and three-dimensional movement of the workpiece. A more efficient actuator is the result, due to the use of the permanent magnets. Various drive signals can be used, so that one portion of the armature will make a slow movement, while the other portion a fast movement, resulting in a variety of different actions of the workpiece. This device can also be operated in a resonant mode.

Figure 8:
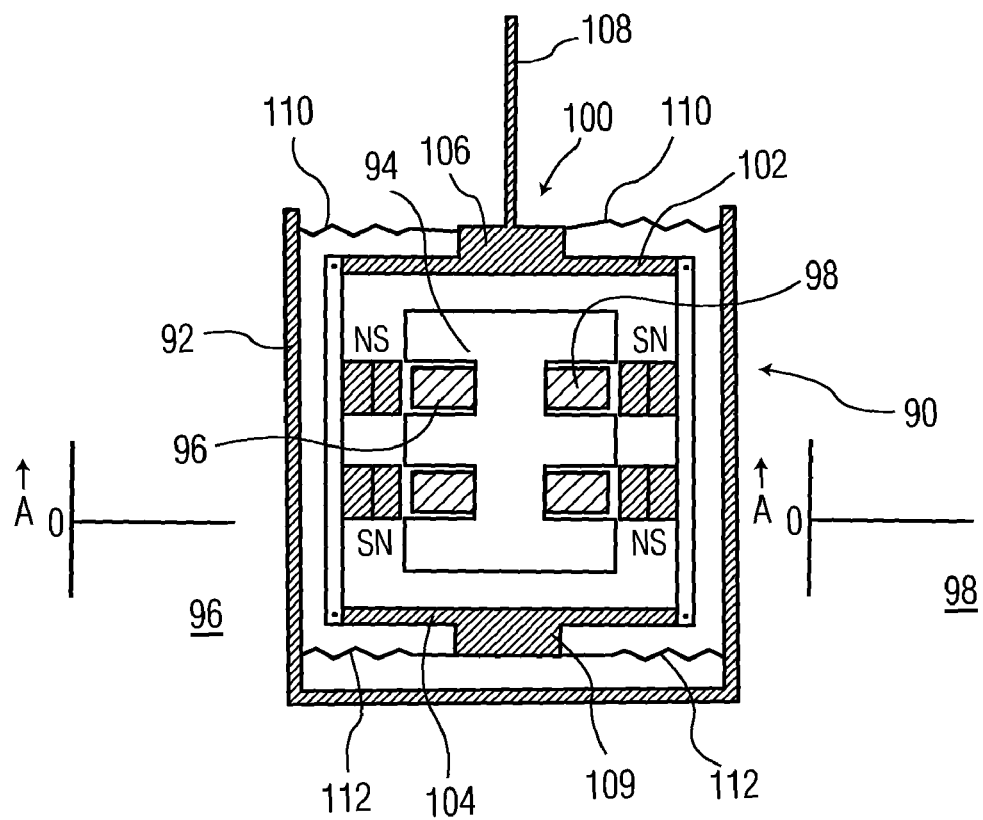
FIG. 8 is a cross-sectional view of a further embodiment of the actuator.

FIG. 8 shows an embodiment similar to that of FIG. 5, but smaller, which makes it more suitable for a toothbrush or similar small appliance application.

The actuator 90 includes a housing 92, a double (back-to-back) E shaped yoke 94, with two coils 96 and 98 wound on the opposing "E" sections. Other yoke configurations can be used. Fewer or greater numbers of coils can also be used. Actuator 90 includes an armature 100, the armature including top and bottom plate-like portions 102 and 104. A mounting block 106 is secured to the upper surface of the top plate 102. A drive shaft 108 extends from mounting block 106. A mounting block 109 is secured to the lower surface of bottom plate 104. Spring members 110 connect mounting block 106 to the housing 92, as shown, while spring members 112 connect mounting block 109 to housing 92. Actuator 90 is not otherwise connected to the housing.

Figure 9A:
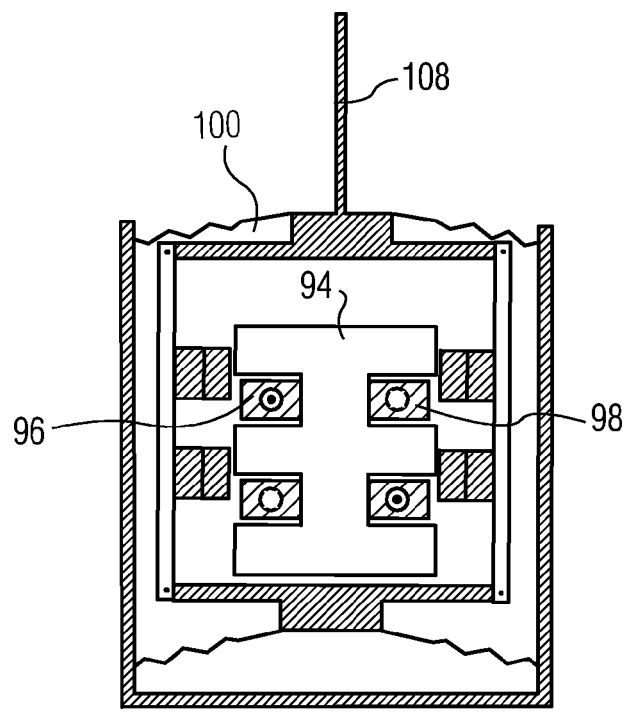
FIGS. 9A and 9B and 10A and 10B show various movements of the actuator of FIG. 8.
Figure 9B:
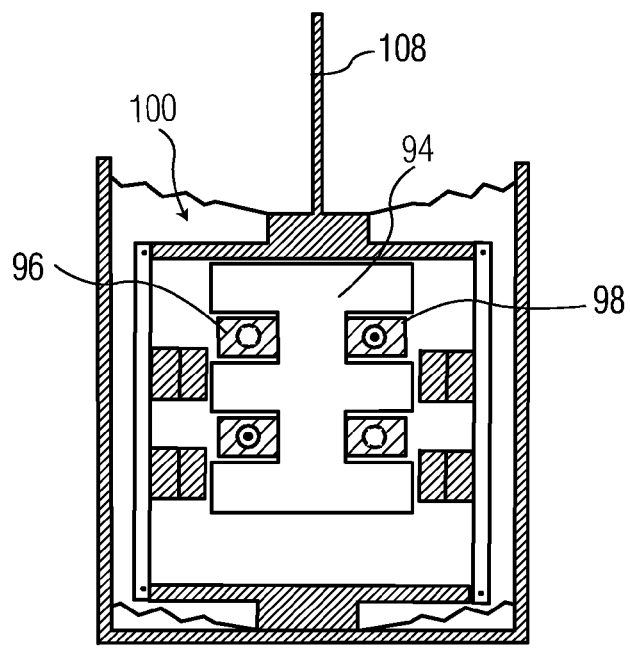
Figure 10A:
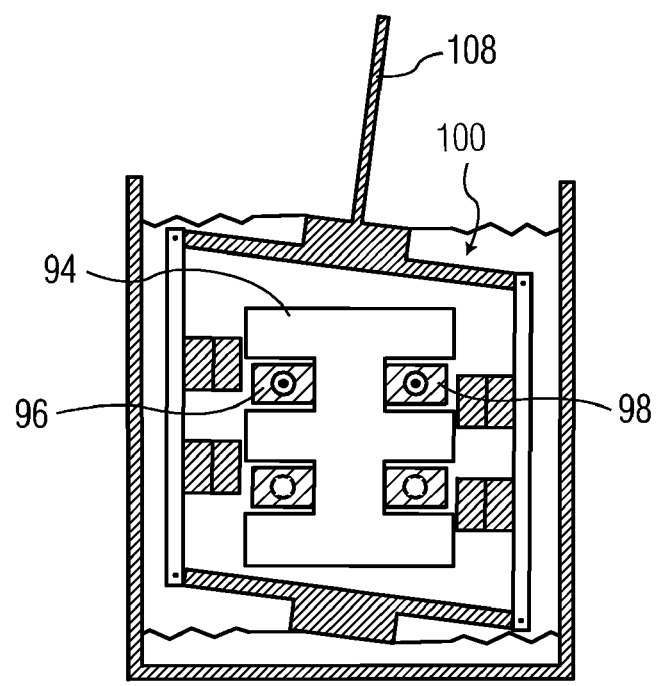
Figure 10B:
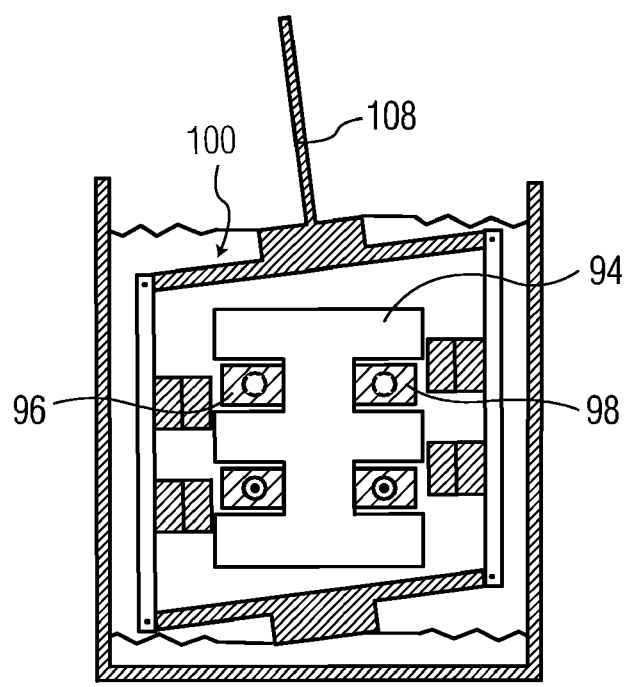

FIGS. 9A and 9B show axial movement (in-and-out) of the actuator (and drive shaft 108) in the "Y" direction relative to the housing when current is applied to the two coils in opposing directions, as shown. When the currents reverse, the actuator changes direction. FIGS. 10A and 10B show actuator (and drive shaft) movement in the "X" direction when a current is applied to only one of the coils or both coils in the same direction, as shown. Reversal of the current(s) results in back and forth movement in the "X" direction.

A significant advantage of the above arrangements is that it is possible to program complex motions of the workpiece in the XY plane. Tangential movement and/or axial movement, as well as complex movements involving both tangential and axial movement, are possible by varying the direction, frequency and magnitude of the drive currents to the coils in the actuator. Two-dimensional and three-dimensional workpiece movements are possible. This can be done by program control.

Although a primary use of the actuator is for power toothbrushes, it should be understood that it can be used in other personal care appliances, such as shavers, trimmers or dipilators.

Although preferred embodiments of the invention have been disclosed for purposes of illustration, it should be understood that various changes, modifications and substitutions may be incorporated in the embodiments without departing from the spirit of the invention which is defined by the claims which follow.

What is claimed is:

1. An actuator mechanism for a personal care appliance having a housing, comprising:

A yoke assembly having two or more spaced outer coil support legs and an intermediate workpiece support leg wherein the outer and intermediate support legs extend in an axial dimension between first ends and opposing free ends thereof;

an armature positioned adjacent the free ends of the support legs of the yoke assembly;

a spring assembly connecting the armature to the housing of the personal care appliance;

an output drive shaft extending from the armature member adapted to receive a workpiece mounting shaft and/or a workpiece member at a free end thereof;

at least one coil wound on the coil support legs of the yoke assembly;

a source of power for the actuator mechanism; and a programmable control system for applying power to the coils to move the armature and the output drive shaft in at least two dimensions, including said axial dimension and a second dimension which is different than the axial dimension.

2. The actuator mechanism of claim 1, wherein the yoke assembly is E-shaped, and wherein coils are wound on each support leg of the E-shaped yoke.

3. The actuator mechanism of claim 1, wherein the programmable control system applies power to the coils in such a manner that the armature and the output drive shaft move in three dimensions.

4. The actuator mechanism of claim 2, wherein when current is applied to the two coils in an equal magnitude, the armature moves toward and away from the yoke assembly in one dimension and wherein when current is applied through only one or the other of the coils, the armature moves tangentially relative to the yoke assembly in an orthogonal dimension.

5. The actuator mechanism of claim 1, wherein the actuator is a part of a power toothbrush and the workpiece is a brushhead.

6. The actuator mechanism of claim 1, wherein the armature is supported by the spring assembly such that when the armature is at rest, there is a small air gap between the armature and the free ends of the legs of the E-shaped yoke.

7. The actuator of claim 1, wherein the armature is a plate member having a central protrusion extending from the lower surface which fits into a receiving notch in the intermediate leg of the yoke assembly, so that in operation, the armature tilts about the intermediate leg in said second dimension which is perpendicular to said axial dimension.

8. An actuator for a personal care appliance, which includes a housing, comprising:

a yoke assembly which includes at least two coils mounted thereon, the yoke assembly having first and second opposing ends, wherein the yoke assembly extends in a Y dimension between said first and second opposing ends;

an armature assembly, comprising a top portion which extends above and over the top of the yoke assembly, adjacent one of said first and second opposing ends thereof, and two depending side portions which extend downwardly past the two coils of the yoke assembly, the depending portions having first and second spaced magnet assemblies secured thereto, aligned with the corresponding electrical coils when the actuator is in a rest position, wherein energizing the coils causes a corresponding movement of the armature;

at least one spring assembly which tends to orient the armature to said rest position;

a source of power for application to the coils; and a programmable control system for applying power to the coils manner to accomplish movement of the actuator, wherein current applied to both coils in opposing directions results in movement of the armature assembly in the Y dimension upon successive reversals of the current, and wherein current applied through one or both coils in the same direction results in movement of the armature in an X dimension which is different than the Y dimension upon successive reversals of the current.

9. The actuator assembly of claim 8, wherein the yoke assembly is mounted to the housing, and wherein the armature includes a top portion which is supported slightly away from the top of the E-shaped yoke, and wherein the spring assemblies extend from approximately the top and bottom of the side portions of the armature to the housing.

10. The actuator assembly of claim 8, wherein the actuator assembly is part of a toothbrush structure, and further includes a brushhead element positioned on the outer end of the mounting shaft.

11. The actuator assembly of claim 8, wherein the armature includes a top plate portion, a bottom plate portion, and wherein the two side portions extend between the peripheral edges of the top and bottom portions, wherein the armature further includes an upper mounting block connected to the top plate portion and a lower mounting block connected to the bottom plate portion, and wherein the top and bottom spring assemblies, respectively, extend between the upper and lower mounting blocks and the housing.

* * * * *